(12) United States Patent
Kim et al.

(10) Patent No.: US 7,959,989 B2
(45) Date of Patent: Jun. 14, 2011

(54) CYCLIC OLEFINS COMPOUNDS, POLYMERS COMPRISING THE SAME AND LIQUID CRYSTAL ALIGNMENT FILMS INCLUDING THE POLYMERS

(75) Inventors: Heon Kim, Daejeon Metropolitan (KR); Sung-Ho Chun, Daejeon Metropolitan (KR); Hee-Jin Lee, Daejeon Metropolitan (KR); Dmitry Kravchuk, Daejeon Metropolitan (KR); Kyung-Jun Kim, Daejeon Metropolitan (KR); Sang-Kook Kim, Seoul (KR); Sung-Joon Oh, Daejeon Metropolitan (KR); Hye-Ran Seong, Seoul (KR); Byung-Hyun Lee, Daejeon Metropolitan (KR); Hye-Won Jeong, Daejeon Metropolitan (KR); Jung-Ho Jo, Suwon-si (KR); Yun-Jeong Lee, Daejeon Metropolitan (KR); Dong-Hyun Oh, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 12/448,198

(22) PCT Filed: Mar. 6, 2008

(86) PCT No.: PCT/KR2008/001288
§ 371 (c)(1),
(2), (4) Date: Nov. 16, 2009

(87) PCT Pub. No.: WO2008/108592
PCT Pub. Date: Sep. 12, 2008

(65) Prior Publication Data
US 2010/0076166 A1    Mar. 25, 2010

(30) Foreign Application Priority Data

Mar. 6, 2007 (KR) ........................ 10-2007-0022164

(51) Int. Cl.
C09K 19/38 (2006.01)
C08F 136/20 (2006.01)
C07C 69/52 (2006.01)
C08F 4/70 (2006.01)

(52) U.S. Cl. ......... 428/1.2; 522/151; 522/152; 522/154; 526/172; 526/273; 526/279; 526/282; 560/45; 560/194; 564/182; 564/383; 568/665; 568/667

(58) Field of Classification Search .................. 526/172, 526/273, 282, 279; 522/151, 152, 154; 428/1.2; 560/45, 194; 564/182, 383; 568/665, 667
See application file for complete search history.

(56) References Cited

U.S. PATENT DOCUMENTS

| | | |
|---|---|---|
| 2002/0132880 A1 | 9/2002 | Choi et al. |
| 2006/0160970 A1 | 7/2006 | Kim et al. |
| 2006/0188806 A1 | 8/2006 | Lee et al. |

FOREIGN PATENT DOCUMENTS

JP    11-181127    7/1999

OTHER PUBLICATIONS

Rehab, Ahmed; "Studies of Photoreactive Poly(Norbornene Derivatives) Bearing Chalcone Units"; Journal of Macromolecular Science; Jul. 2003, vol. A40, No. 7, pp. 789-703, ISSN 1520-5738; See abstract; Scheme 1; p. 793, preparation of polymers.

*Primary Examiner* — Fred M Teskin
(74) *Attorney, Agent, or Firm* — McKenna Long & Aldridge LLP (57) ABSTRACT

The present invention relates to a novel cyclic olefin compound, a polymer including the cyclic olefin compound, a liquid crystal alignment film including the polymer, and a liquid crystal display device including the liquid crystal alignment film. Since the polymer includes the cyclic olefin compound as a main chain, the thermal stability is excellent and the photoreactive speed is high. Accordingly, the production time can be reduced, the production cost can be reduced, and the anchoring force of the liquid crystal can be increased because the alignment property is stabilized due to the curing.

23 Claims, 2 Drawing Sheets

CYCLIC OLEFINS COMPOUNDS, POLYMERS COMPRISING THE SAME AND LIQUID CRYSTAL ALIGNMENT FILMS INCLUDING THE POLYMERS

TECHNICAL FIELD

The present invention relates to a cyclic olefin compound, a polymer including the cyclic olefin compound, a liquid crystal alignment film including the polymer, and a liquid crystal display device including the liquid crystal alignment film.

This application claims priority from International Application No. PCT/KR2008/001288, filed on Mar. 6, 2008, and Korean Patent Application No. 10-2007-0022164 filed on Mar. 6, 2007 in the KIPO, both of which are incorporated herein by reference in its entirety.

BACKGROUND ART

In recent years, a liquid crystal display which has a light weight and consumes a small amount of electric power has been used as a most competitive display that can be used instead of a cathode ray tube. In particular, since a thin film transistor liquid crystal display (TFT-LCD) that is driven by using a thin film transistor independently drives each of pixels, a response speed of the liquid crystal is very high, thus, a high-quality dynamic image can be realized. Accordingly, currently, the thin film transistor liquid crystal display is applied to a notebook computer, a wall-mounted television and the like, and the application range thereof is expanded.

During the production of a typical color thin film transistor-liquid crystal display, a thin film transistor driving device and an ITO transparent electrode are layered on a glass substrate, and an alignment film is then layered thereon to form a lower substrate of a cell. Spacers are formed by using a silant in order to inject a liquid crystal material between inner surfaces of a pair of upper and lower substrates, polarized films are provided on outer surfaces of the glass substrates, and the liquid crystal material is injected between a pair of substrates and cured to produce a liquid crystal display cell.

In the TFT-LCD, in order to use the liquid crystal as an optical switch, it is required that the liquid crystal is initially aligned on the layer on which the thin film transistor is formed at the innermost part of the display cell in a predetermined direction. In order to achieve this, a liquid crystal alignment film is used.

With respect to a method for producing the alignment film, in the related art, a polymer film such as polyimide is applied on a substrate such as glass and the like, and the surface is subjected to a rubbing process by using a fiber such as nylon or polyester in a predetermined direction. However, the rubbing process may cause fine dust or static electricity when the fibroid material is rubbed in conjunction with the polymer film, which may cause a serious problem during the production of the liquid crystal panel.

In order to avoid the problem of the rubbing process, in recent years, an optical alignment process has been studied to radiate light instead of using the rubbing so that anisotropy is induced to the polymer film to align the liquid crystal. The optical alignment anisotropically occurs by reactions such as light isomerization and photocrosslinking of a photosensitive group that is connected to the polymer due to linearly polarized ultraviolet rays. Accordingly, in the optical alignment process, the liquid crystals may be unidirectionally aligned by providing the anisotropy to the surface of the polymer by using the ultraviolet rays.

The polycinnamate-based polymer such as PVCN (poly (vinyl cinnamate)) and PVMC (poly(vinyl methoxycinnamate)) has been mainly used as a representative material of the optical alignment film. However, the polycinnamate-based polymer has a problem in that the optical alignment property of the polymer is excellent but the thermal stability is poor.

For example, Japanese Unexamined Patent Application Publication No. 11-181127 discloses a method of producing a polymer-type alignment film that has a main chain such as acrylate and methacrylate and a side chain having a photosensitive group such as a cinnamate group, and an alignment film produced by using the method. However, the patent is disadvantageous in that since the mobility of the polymer is poor, even though the polymer is exposed to light for a long time, it is difficult to obtain the desired alignment property. The reason for this is that since the photosensitive group which is present in the polymer is restricted by the main chain of the polymer, the group is difficult to rapidly react with the radiated polarized light. Accordingly, since a long time is required to obtain a network polymer, process efficiency is reduced, and if an alignment treatment is not processed with sufficient time, a plurality of unreacted photofunctional groups reduce the light stability and the thermal stability. Therefore, in the case of the liquid crystal display device produced by using the polymer, since the alignment of the liquid crystal is insufficient, a dichroic ratio is low, contrast is reduced, and the anchoring force is reduced. Thus, there is a disadvantage in that it is difficult to obtain a high quality image.

DISCLOSURE

Technical Problem

Accordingly, the present invention has been made keeping in mind the problems occurring in the related art, and an object of the present invention is to provide a cyclic olefin compound that has the excellent thermal stability, the improved photoreactive speed, and the excellent anchoring force, and a polymer that includes the cyclic olefin compound. Another object of the present invention is to provide a liquid crystal alignment composition that includes the polymer, a liquid crystal alignment film produced by using the liquid crystal alignment composition, and a liquid crystal display device that includes the liquid crystal alignment film.

Technical Solution

The present invention provides a novel cyclic olefin compound.

In addition, the present invention provides a polymer that includes the cyclic olefin compound.

In addition, the present invention provides a method for producing the polymer.

In addition, the present invention provides a liquid crystal alignment composition that includes the polymer.

In addition, the present invention provides a liquid crystal alignment film that is produced by using the liquid crystal alignment composition.

In addition, the present invention provides a method for producing the liquid crystal alignment film.

In addition, the present invention provides a liquid crystal display device that includes the liquid crystal alignment film.

Advantageous Effects

The polymer according to the present invention includes the cyclic olefin compound having both the photoreactive group and the curable functional group. Accordingly, since the glass transition temperature is high, the thermal stability is excellent. Furthermore, since a vacant lattice area is relatively large, the photoreactive group can be relatively freely moved. Thus, the polymer according to the present invention is characterized in that since the photoreactive speed is high as compared to a known polymer for alignment film production used to produce the liquid crystal display device, the production time is reduced, the production cost can be reduced, and the anisotropy generated after the photoreaction is stabilized because of the curing reaction to increase the alignment regulation strength.

DESCRIPTION OF DRAWINGS

The above and other features and advantages of the present invention will become more apparent by describing in detail preferred embodiments thereof with reference to the attached drawings in which.

MODE FOR INVENTION

Hereinafter, a detailed description will be given of the present invention.

A cyclic olefin compound according to the present invention is represented by the following Formula 1.

[Formula 1]

In the above Formula 1, P is an integer in the range of 0 to 4, and at least one of R1, R2, R3, and R4 is a radical that is represented by the following Formula 2.

[Formula 2]

In the above Formula 2, m is an integer in the range of 1 to 5,

A is any one selected from substituted or unsubstituted linear or brached alkylene having 1 to 20 carbon atoms; carbonyl; and substituted or unsubstituted arylene or haloarylene having 6 to 40 carbon atoms, B and B' are the same as or different from each other, and oxygen or nitrogen,

R9 is any one selected from a direct bond, linear or brached alkylene or haloalkylene having 1 to 20 carbon atoms; linear or brached alkenylene or haloalkenylene having 2 to 20 carbon atoms; substituted or unsubstituted cycloalkylene or halocycloalkylene having 5 to 12 carbon atoms; substituted or unsubstituted haloarylene having 6 to 40 carbon atoms; substituted or unsubstituted aralkylene or haloaralkylene having 7 to 15 carbon atoms; and alkynylene or haloalkynylene having 2 to 20 carbon atoms, and X is any one selected from functional groups that are represented by the following Formulae 3, 4, and 5.

[Formula 3]

In the above Formula 3, * means a connection unit, and R10 is hydrogen; or an alkyl or cycloalkyl group having 1 to 4 carbon atoms.

[Formula 4]

In the above Formula 4, * means a connection unit, and n is an integer in the range of 1 to 9.

[Formula 5]

In the above Formula 5, n is an integer in the range of 0 to 9, among R1, R2, R3, and R4, the remainders other than the group that is represented by Formula 2 are each independently selected from hydrogen; halogen; linear or branched alkyl that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy; halocarbonyloxy, aryloxy, haloaryloxy, silyl, and siloxy; cycloalkyl that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; aryl that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; and a polar functional group that contains at least one of oxygen, nitrogen, phosphorus, sulfur, silicon, and boron, and

R1 and R2 or R3 and R4 may be bonded to each other to form an alkylidene group having 1 to 10 carbon atoms or R1 or R2 may be bonded to any one of R3 and R4 to form a saturated or unsaturated aliphatic ring having 4 to 12 carbon atoms or an aromatic ring having 6 to 24 carbon atoms.

Specific examples of the polar functional group may include $R_5OR_6$, —$OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$ (p is an integer in the range of 1 to 10), —$(OR_5)_p$—$OR_6$ (p is an integer in the range of 1 to 10), —$C(O)$—$O$—$C(O)R_6$, —$R_5C(O)$—$O$—$C(O)R_6$, —$SR_6$, —$R_5SR_6$, —$SSR_6$, —$R_6SSR_6$, —$S(=O)R_6$, $R_5S(=O)R_6$, —$R_5C(=S)R_6$, —$R_5C(=S)SR_6$, —$R_5SO_3R_6$, —$SO_3R_6$, $R_5N=C=S$, —$N=C=S$, —$NCO$, —$R_5$—$NCO$, —$R_5CN$, —$NNC(=S)R_6$, —$R_5NNC(=S)R_6$, -continued In the polar functional group, $R_5$ is linear or branched alkylene that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenylene that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynylene that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkylene that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; arylene that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; or alkoxylene that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; two or more $R_5$s are the same as or different from each other when two or more $R_5$s are present, and

$R_6$, $R_7$, and $R_8$ are the same as or different from each other, and hydrogen; halogen; linear or branched alkyl that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkyl that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; aryl that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; or alkoxy that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy.

The cyclic olefin compound that is represented by the above Formula 1 may be any one cyclic olefin compound that is selected from the group consisting of compounds that are represented by the following Formulae 6 to 8.

[Formula 6]

[Formula 7]

[Formula 8]

The present invention provides a method for producing the cyclic olefin compound.

In the method for producing the cyclic olefin compound, after a cyclic olefin compound including a hydroxy group, halides, amine or the like and the photoreactive functional compound including the hydroxy group and the photoreactive group simultaneously are bonded to each other, the hydroxy group that is bonded to an end of the photoreactive group is substituted by the photoreactive or curable functional group.

In addition, the present invention provides a polymer that includes the cyclic olefin compound. The polymer according to the present invention is the photoreactive polymer, and includes the cyclic olefin compound having the photoreactive group in conjunction with the curable functional group. In the case of the photoreactive polymer having the cyclic olefin compound in a main chain thereof, since the glass transition temperature is high, the thermal stability is excellent. Furthermore, since a vacant lattice area is relatively large, the photoreactive group can be relatively freely moved. Accordingly, the photoreactive polymer according to the present invention is characterized in that since the photoreactive speed is high as compared to a known polymer for alignment film production used to produce the liquid crystal display device, the production time is reduced, the production cost can be reduced, and the anisotropy generated after the photoreaction is stabilized because of the curing reaction to increase the anchoring force.

In connection with this, it is preferable that the polymer include a repeating unit that is represented by the following Formula 9.

[Formula 9]

In the Formula 9,
n is in the range of 50 to 5,000, and
R1 to R4 and p are the same as those defined by Formula 1.

The polymer according to the present invention may further include any one that is selected from the group consisting of the repeating unit that is represented by the following Formula 10 and a repeating unit that is derived from the linear olefins. In connection with this, the repeating unit that is derived from the linear olefins means a repeating unit that has a double bond connected to a main chain thereof, which can be easily understood by those who skilled in the art.

[Formula 10]

In Formula 10,
p is an integer in the range of 0 to 4,
R1', R2', R3', and R4' are each independently selected from hydrogen; halogen; linear or branched alkyl that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkyl that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; aryl that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; and a polar functional group that contains at least one of oxygen, nitrogen, phosphorus, sulfur, silicon, and boron, and R1' and R2' or R3' and R4' may be bonded to each other to form an alkylidene group having 1 to 10 carbon atoms or R1' or R2' may be bonded to any one of R3' and R4' to form a saturated or unsaturated aliphatic ring having 4 to 12 carbon atoms or an aromatic ring having 6 to 24 carbon atoms.

Examples of the polar functional group are the same as those that are defined by the above Formula 1.

In the case of when the polymer according to the present invention includes the repeating unit represented by Formula 9 and the repeating unit represented by Formula 10, it is preferable that the polymer according to the present invention includes 1 to 99 mol % of the repeating unit represented by Formula 9 and 1 to 99 mol % of the repeating unit represented by Formula 10 and the degree, of polymerization of the polymer be in the range of 50 to 5000.

In connection with this, in the case of when the content of the repeating unit represented by Formula 10 is less than 1 mol %, there is a problem in that the solubility of the polymer is reduced. In the case of when the content of the repeating unit represented by Formula 10 is more than 99 mol %, there is a problem in that the photoreactive speed is lowered due to the low content of the photoreactive functional group. This is undesirable.

The linear olefin may be selected from α-olefin, butadiene, and pentadien having 1 to 20 carbon atoms.

The polymer according to the present invention may be a polymer including the repeating unit that is represented by the following Formula 11 through the ring-opening substitution polymerization reaction of the cyclic olefin compound.

[Formula 11]

In Formula 11, n, p, and R1 to R4 are the same as those that are defined by Formula 9.

The present invention provides a method for producing a polymer that includes the cyclic olefin compound as a monomer. Specifically, the method includes performing the polymerization at the temperature in the range of 10 to 200° C. in the presence of the catalyst mixture that includes the precatalyst containing the transition metal of Group X and the cocatalyst providing the Lewis base capable of being weakly coordinated with the metal of the precatalyst. In connection with this, in the case of when the reaction temperature is less than 10° C., there is a problem in that the polymerization activity is very low. In the case of when the reaction temperature is more than 200° C., there is a problem in that the catalyst is decomposed. This is undesirable.

In the method for producing the polymer according to an embodiment of the present invention, after the catalyst mixture that includes the precatalyst containing the transition metal of Group X and the cocatalyst providing the Lewis base capable of being weakly coordinated with the metal of the precatalyst is produced, the monomer solution that includes the cyclic olefin compound represented by Formula 1 may be subjected to the addition polymerization reaction in the presence of the organic solvent and the catalyst mixture to prepare the polymer according to the present invention. In connection with this, the addition order of the catalyst, the monomer, and the solvent are not limited.

The catalyst mixture may include 1 to 1000 mole of the cocatalyst providing the Lewis base capable of being weakly coordinated with the metal of the precatalyst in respects to 1 mole of the precatalyst containing the transition metal of Group X. If the content of the cocatalyst is less than 1 mole, the catalyst activity cannot be obtained. If the content of the cocatalyst is more than 1000 mole, there is a problem in that the catalyst activity is reduced. This is undesirable.

In connection with this, the catalyst mixture may further include a compound containing a neutral electron donor ligand of Group XV, which may be a compound represented by the following Formula 12.

$[P(R)_3]$ [Formula 12]

In Formula 12,

R is any one selected from the group consisting of hydrogen; linear or brached alkyl or alkoxy having 1 to 20 carbon atoms; linear or brached alkenyl having 2 to 20 carbon atoms; substituted or unsubstituted cycloalkyl having 3 to 12 carbon atoms; substituted or unsubstituted aryl having 6 to 40 carbon atoms; substituted or unsubstituted aralkyl having 7 to 15 carbon atoms; and alkynyl having 2 to 20 carbon atoms, and two or more Rs are the same as or different from each other when two or more Rs are present. In connection with this, each of the substituent groups may be substituted by halogen or haloalkyl having 1 to 20 carbon atoms.

Specifically, examples of the compound that contains a neutral electron donor ligand of Group XV include one or more selected from tricyclohexyl phosphine, triisopropyl phosphine, triphenyl phosphine, tri-t-butyl phosphine, and dicyclohexyl-t-butyl phosphine.

Examples of the precatalyst include one or more selected from $[(Allyl)Pd(Cl)]_2$, $[Pd(acetate)_2]$, $[NiBr(NPMe)_3]_4$, and $[PdCl(NB)OMe]_2$.

Examples of the cocatalyst include one or more selected from borane, borate, alkyl aluminum, and transition metal halide.

Specific examples of the cocatalyst include one or more selected from $B(C_6F_5)_3$, dimethylanilinium tetrakis(pentafluorophenyl)borate, methyl aluminoxane (MAO), triethyl aluminum $[Al(C_2H_5)_3]$, and $AgSbF_6$.

The present invention provides a liquid crystal alignment composition including the polymer.

The liquid crystal alignment composition may further include one or more selected from the group consisting of a photoinitiator, a multicrosslinker, and a mixture thereof in addition to the polymer according to the present invention.

The present invention provides a liquid crystal alignment film that is produced by using the liquid crystal alignment composition. In connection with this, the liquid crystal alignment film may be produced by applying the solution including the liquid crystal alignment composition on a substrate having a transparent electrode, removing a solvent to form a film, radiating ultraviolet rays that are polarized in a predetermined direction to provide the anisotropy on the surface of the film, and curing the resulting film.

In addition, the present invention provides a liquid crystal display device that includes the liquid crystal alignment film.

In the present specification, it is preferable that aryl include, for example, phenyl, naphthyl, biphenyl, terphenyl, triphenylenyl, anthryl, phenanthrenyl, phenalenyl, quarterphenyl, pyrenyl, chrysenyl, tetracenyl, tetraphenyl, tetraphenylenyl, perylenyl, pentacenyl, pentaphenyl, picenyl, fluorenyl, indacenyl, biphenylenyl, acenaphthylenyl, acephenanthrenyl, tetralinyl, indenyl, stilbenyl, coronenyl and the like.

In addition, in the present specification, the term 'substituted or unsubstituted' means substitution or unsubstitution by using halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, siloxy or the like.

Alkenyl may include vinyl and allyl.

Hereinafter, the present invention will be described in detail in light of Examples. The present invention may, however, be embodied in many different forms and should not be construed as being limited to the Examples set forth herein. Rather, these Examples are provided such that this disclosure will be thorough and complete and will fully convey the concept of the present invention to those skilled in the art.

All operations that treats compounds that are sensitive to air or water in the following Examples were performed by using a standard Schlenk technique. The nuclear magnetic resonance (NMR) spectrum was measured by using the Bruker 400 spectrometer. In connection with this, $^1$H NMR was measured at 400 MHz, and $^{13}$C NMR was measured at 75 MHz. The molecular weight and the molecular weight distribution of the polymer were measured by using the GPC (gel permeation chromatography). In connection with this, the polystyrene sample was used as the standard. Toluene was distilled by using potassium/benzophenone to perform the distillation, and dichloromethane was distilled and purified by using $CaH_2$.

Example 1

Synthesis of the Allyl Oxy Cinnamate Norbornene (Formula 8) Monomer 1-(1): Synthesis of Allyl Oxy Benzaldehyde After 4-hydroxy benzaldehyde (20 g, 0.164 mol) was dissolved in 200 ml of acetone, allyl bromide (30 g, 0.246 mol) and $K_2CO_3$ (34 g, 0.246 mol) were added, and the refluxing was performed at 65° C. overnight. Next, the resulting mixture was cooled to normal temperature, and the filtering was performed by using acetone. The filtrate was extracted by using ethyl acetate and then subjected to work-up to obtain 27.1 g of the yellow oil product. The amount was an amount that exceeds the yield of 100%. Even though a small amount of impurity was present, the subsequent reaction was performed in an oil state.

1-(2): Synthesis of the Allyl Oxy Cinnamic Acid

Pyridine (50 g, excess as solvent) and the small amount of piperidine were added to the malonic acid (35 g, 0.336 mol), and then agitated for 15 min to completely dissolve the acid. Next, allyl oxy benzaldehyde (26.6 g, the value calculated while the theoretical value of the compound of 1-(1) was considered to be 100%) was added thereto, and then heated to 90° C. The $CO_2$ gas, which was the byproduct of the reaction, was vigorously generated and the reaction was finished after 2 hours. The resulting substance was quenched by using the diluted HCl aqueous solution, and then subjected to work-up by using ethyl acetate. When the solvent was removed, a yellow solid product was obtained. The yellow solid product was recrystallized by using ethyl acetate and n-hexane and then purified to obtain the desired product in an amount of 25 g (yield: 75%).

1-(3): Synthesis of the Allyl Oxy Cinnamate Norbornene

The allyl oxy cinnamic acid (10.8 g, 52.9 mmol) synthesized in Example 1-(2), norbornene methanol (6.5 g, 52.4 mmol), EDC (Aldrich, Inc., 16 g, 84 mmol), and HOBT (Aldrich, Inc., 10.6 g, 78 mmol) were added to the 2-neck flask having the volume of 250 ml, and dissolved in 100 ml of DMF. After the temperature was reduced to 0° C., triethylamine (Aldrich, Inc., 21 g, 0.21 mol) was slowly dropped thereon. After the reaction was performed overnight while the temperature was increased to normal temperature, the reaction was finished and the extraction was performed by using a large amount of ethyl acetate. After the washing was performed by using $NaHCO_3$ and $H_2O$ and the drying was performed by using anhydrous $MgSO_4$, the filtration was performed to remove the solvent by using a rotary evaporator, thus creating the product. The purification was performed by using the column chromatography (Hexane:Ethyl acetate=10:1) to obtain 12.75 g of pure allyl oxy cinnamate norbornene (yield: 78.4%).

The above-mentioned procedure is shown in the following Reaction Equation 1.

Figure 1:
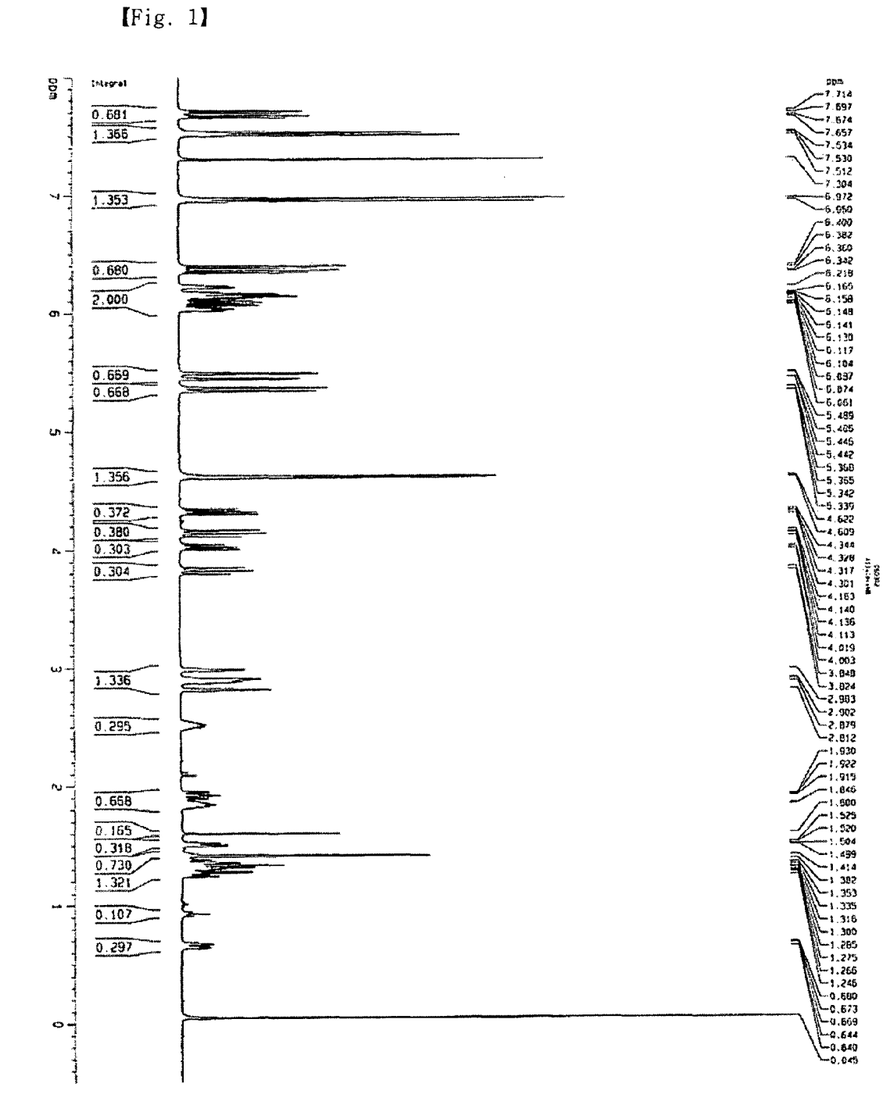
FIG. 1 is a graph that illustrates an NMR result of a compound that is produced in Example 1 of the present invention.

The NMR analysis was performed in order to confirm that allyl oxy cinnamate norbornene represented by Formula 8 was generated, and the results are shown in FIG. 1.

Example 2

Synthesis of the Allyl Oxy Cinnamate Norbornene (Formula 8) Polymer

Allyl oxy cinnamate norbornene (12.75 g, 41.1 mmol) used as the monomer and 65 ml of toluene that was purified with the solvent were added to the Schlenk flask having the volume of 250 ml. Pd(OAc)$_2$ (1.8 ml, 8.216 μmol and tricyclohexyl phosphonium(tetrakispentafluorophenyl) borate ([(Cy)$_3$PH][B(C$_6$F$_5$)$_4$]) (15.8 mg, 16.432 μmol) that were dissolved in 3 ml of dichloromethane were added to the flask as the catalyst, and reacted with each other while the agitation was performed at 90° C. for 18 hours. The reactants were diluted with 65 ml of toluene 18 hours after the reaction was started, and then added to an excessive amount of ethanol to obtain a white polymer precipitate. The precipitate was filtered and recovered by using a glass funnel, and dried in a vacuum oven at 65° C. for 24 hours to obtain 8 g of the allyl oxy cinnamate norbornene polymer (Mw=152,000, PDI=2.71, and yield=63%).

Example 3

Synthesis of the 2,3-epoxy-1-propoxy cinnamate norbornene (Formula 7) monomer 3-(1): 4-hydroxy cinnamate norbornene The 4-hydroxy cinnamic acid (8.7 g, 53 mmol), norbornene methanol (6.5 g, 52.4 mmol), EDC (Aldrich, Inc., 16 g, 84 mmol), and HOBT (Aldrich, Inc., 10.6 g, 78 mmol) were added to the 2-neck flask having the volume of 250 ml, and dissolved in 100 ml of DMF. After the temperature was reduced to 0° C., triethylamine (Aldrich, Inc., 21 g, 0.21 mol) was slowly dropped thereon. After the reaction was performed overnight while the temperature was increased to normal temperature, the reaction was finished and the extraction was performed by using a large amount of ethyl acetate. After the washing was performed by using NaHCO$_3$ and H$_2$O and the drying was performed by using anhydrous MgSO$_4$, the filtration was performed to remove the solvent by using a rotary evaporator, thus creating the product. The purification was performed by using the column chromatography (Hexane:Ethyl acetate=15:1) to obtain 9.9 g of pure product (yield: 70%).

3-(2): Synthesis of 2,3-epoxy-1-propoxy cinnamate norbornene (Formula 7)

Figure 2:
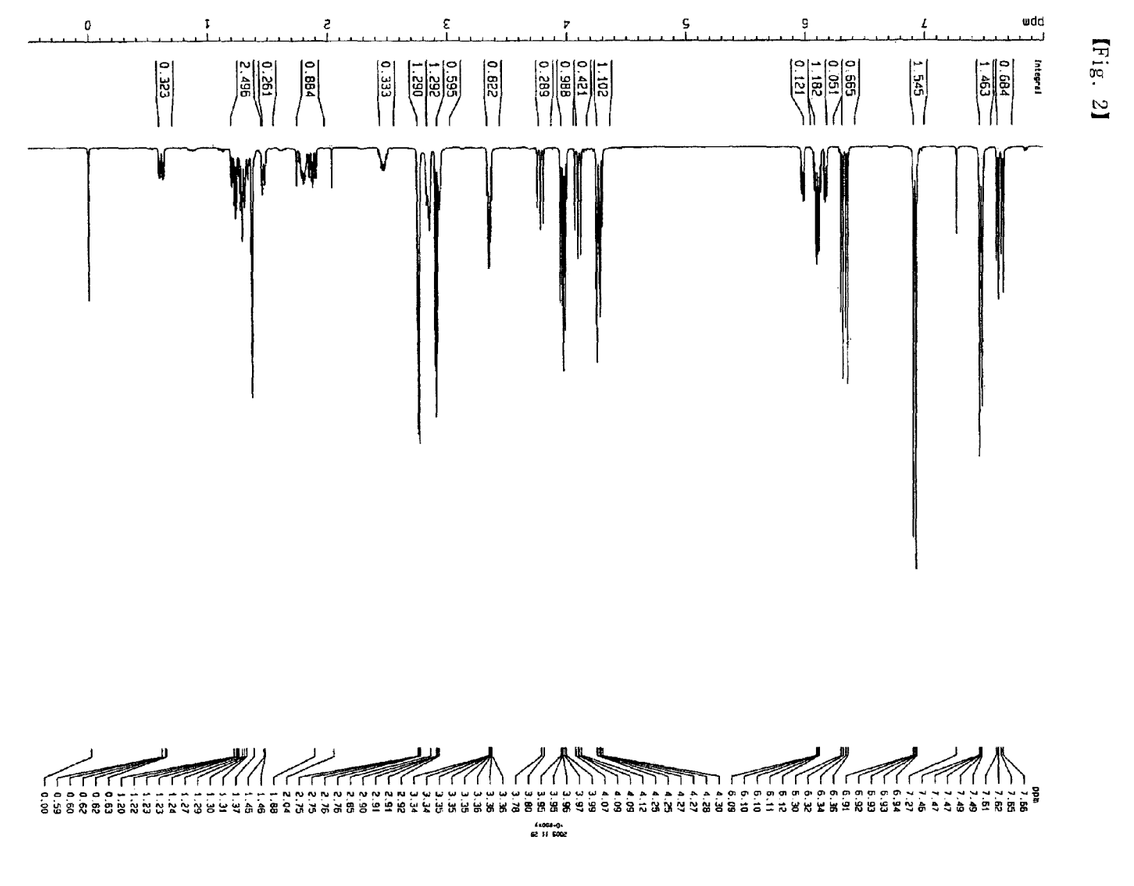
FIG. 2 is a graph that illustrates an NMR result of a compound that is produced in Example 3 of the present invention.

After 4-hydroxy cinnamate norbornene (10 g, 37 mmol) was dissolved in 100 ml of acetone, epichlorohydrine (4.1 g, 44.4 mmol) and K$_2$CO$_3$ (5.4 g, 38.8 mmol) were added thereto, and the refluxing was performed at 80° C. overnight. Next, the resulting mixture was cooled to normal temperature, and the filtering was performed by using acetone. The filtrate was extracted by using ethyl acetate and then subjected to work-up to obtain the yellow oil product. The purification was performed by using the column chromatography (Hexane:Ethyl acetate=5:1) to obtain 5 g of pure product (yield: 40%). The NMR analysis was performed in order to confirm that the compound represented by Formula 7 was generated, and the results are shown in FIG. 2.

Example 4

Synthesis of the 2,3-epoxy-1-propoxy cinnamate norbornene (Formula 7) polymer 2,3-epoxy-1-propoxy cinnamate norbornene (8 g, 24.51 mmol) used as the monomer and 32 ml of toluene that was purified with the solvent were added to the Schlenk flask having the volume of 250 ml. Pd(OAc)$_2$ (5.5 mg, 24.5 μmol) and tricyclohexyl phosphonium(tetrakispentafluorophenyl) borate ([(Cy)$_3$PH][B(C$_6$F$_5$)$_4$]) (47.1 mg, 49 μmol) that were dissolved in 3 ml of dichloromethane were added to the flask as the catalyst, and reacted with each other while the agitation was performed at 110° C. for 18 hours. The reactants were diluted with 32 ml of toluene 18 hours after the reaction was started, and then added to an excessive amount of ethanol to obtain a white polymer precipitate. The precipitate was filtered and recovered by using a glass funnel, and dried in a vacuum oven at 65° C. for 24 hours to obtain 3 g of the 2,3-epoxy-1-propoxy cinnamate norbornene polymer (yield=37%).

The invention claimed is:

1. A cyclic olefin compound that is represented by the following Formula 1:

<Formula 1> wherein P is an integer in the range of 0 to 4, and
at least one of R1, R2, R3, and R4 is a radical that is represented by the following Formula 2,

<Formula 2> wherein m is an integer in the range of 1 to 5,
A is any one selected from substituted or unsubstituted linear or branched alkylene having 1 to 20 carbon atoms; carbonyl; and substituted or unsubstituted arylene or haloarylene having 6 to 40 carbon atoms,
B and B' are the same as or different from each other, and oxygen or nitrogen,
R9 is any one selected from a direct bond, linear or branched alkylene or haloalkylene having 1 to 20 carbon atoms; linear or branched alkenylene or haloalkenylene having 2 to 20 carbon atoms; substituted or unsubstituted cycloalkylene or halocycloalkylene having 5 to 12 carbon atoms; substituted or unsubstituted arylene or haloarylene having 6 to 40 carbon atoms; substituted or unsubstituted aralkylene or haloaralkylene having 7 to 15 carbon atoms; and alkynylene or haloalkynylene having 2 to 20 carbon atoms, and
X is any one selected from functional groups that are represented by the following Formulae 3, 4 and 5

<Formula 3> wherein * means a connection unit, and
R10 is hydrogen; or an alkyl having 1 to 4 carbon atoms or cycloalkyl group,

<Formula 4> wherein * means a connection unit, and
n is an integer in the range of 1 to 9,

<Formula 5> wherein n is an integer in the range of 0 to 9,
among R1, R2, R3, and R4, the remainders other than the group that is represented by Formula 2 are each independently selected from hydrogen; halogen; linear or branched alkyl that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkyl that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; aryl that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; and a polar functional group that contains at least one of oxygen, nitrogen, phosphorus, sulfur, silicon, and boron, and
R1 and R2 or R3 and R4 may be bonded to each other to form an alkylidene group having 1 to 10 carbon atoms or R1 or R2 may be bonded to any one of R3 and R4 to form a saturated or unsaturated aliphatic ring having 4 to 12 carbon atoms or an aromatic ring having 6 to 24 carbon atoms.

2. The cyclic olefin compound as set forth in claim 1, wherein the polar functional group comprises compounds represented by the following Formulae:
—$R_5OR_6$, —$OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$ (p is an integer in the range of 1 to 10), —$(OR_5)_p$—$OR_6$ (p is an integer in the range of 1 to 10), —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(\!=\!O)R_6$, —$R_5S(\!=\!O)R_6$, —$R_5C(\!=\!S)R_6$—, —$R_5C(\!=\!S)SR_6$, —$R_5SO_3R_6$, —$SO_3R_6$, —$R_5N\!=\!C\!=\!S$, —$N\!=\!C\!=\!S$, —NCO, —$R_5$—NCO, —CN, —$R_5$CN, —$NNC(\!=\!S)R_6$, —$R_5NNC(\!=\!S)R_6$, —$NO_2$, —$R_5NO_2$, -continued in the polar functional group, $R_5$ is linear or branched alkylene that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenylene that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynylene that has 2 to 20 carbon atoms and is substituted or unsubstituted with one or more substituent groups consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkylene that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; arylene that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; or alkoxylene that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; two or more $R_5$s are the same as or different from each other when two or more $R_5$s are present, and $R_6$, $R_7$, and $R_8$ are the same as or different from each other, and hydrogen; halogen; linear or branched alkyl that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkyl that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; aryl that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; or alkoxy that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy.

3. The cyclic olefin compound as set forth in claim 1, wherein the cyclic olefin compound that is represented by Formula 1 is any one selected from the group consisting of compounds that are represented by the following Formulae 6 to 8:

[Formula 6]

[Formula 7]

[Formula 8]

4. A polymer comprising the cyclic olefin compound according to claim 1.

5. The polymer as set forth in claim 4, comprising:
a repeating unit that is represented by the following Formula 9:

<Formula 9> wherein n is in the range of 50 to 5,000,
and p is an integer in the range of 0 to 4.

6. The polymer as set forth in claim 4, further comprising:
one or more of a repeating unit that is represented by the following Formula 10 and a repeating unit that is derived from a linear olefin:

<Formula 10> wherein p is an integer in the range of 0 to 4, and
R1', R2', R3', and R4' are each independently the same as the remainder other than the groups that are represented by Formula 2 among R1, R2, R3 and R4.

7. The polymer comprising a repeating unit that is represented by the following Formula 11:

<Formula 11> wherein n is in the range of 50 to 5,000, p is an integer in the range of 0 to 4, and at least one of R1, R2, R3, and R4 is a radical that is represented by the following Formula 2:

<Formula 2> wherein m is an integer in the range of 1 to 5,

A is any one selected from substituted or unsubstituted linear or branched alkylene having 1 to 20 carbon atoms; carbonyl; and substituted or unsubstituted arylene or haloarylene having 6 to 40 carbon atoms, B and B' are the same as or different from each other, and oxygen or nitrogen, R9 is any one selected from a direct bond, linear or branched alkylene or haloalkylene having 1 to 20 carbon atoms; linear or branched alkenylene or haloalkenylene having 2 to 20 carbon atoms; substituted or unsubstituted cycloalkylene or halocycloalkylene having 5 to 12 carbon atoms; substituted or unsubstituted arylene or haloarylene having 6 to 40 carbon atoms; substituted or unsubstituted aralkylene or haloaralkylene having 7 to 15 carbon atoms; and alkynylene or haloalkynylene having 2 to 20 carbon atoms, and X is any one selected from functional groups that are represented by the following Formulae 3, 4 and 5, <Formula 3> wherein * means a connection unit, and

R10 is hydrogen; or an alkyl or cycloalkyl group having 1 to 4 carbon atoms,

<Formula 4> wherein * means a connection unit, and n is an integer in the range of 1 to 9,

<Formula 5> wherein n is an integer in the range of 0 to 9, among R1, R2, R3, and R4, the remainders other than the group that is represented by Formula 2 are each independently selected from hydrogen; halogen; linear or branched alkyl that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkyl that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; aryl that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; and a polar functional group that contains at least one of oxygen, nitrogen, phosphorus, sulfur, silicon, and boron, R1 and R2 or R3 and R4 may be bonded to each other to form an alkylidene group having 1 to 10 carbon atoms or R1 or R2 may be bonded to any one of R3 and R4 to form a saturated or unsaturated aliphatic ring having 4 to 12 carbon atoms or an aromatic ring having 6 to 24 carbon atoms, the polar functional group includes compounds represented by the following Formulae:

—$R_5OR_6$, —$OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$ (p is an integer in the range of 1 to 10), —$(OR_5)_p$—$OR_6$ (p is an integer in the range of 1 to 10), —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)R_6$—, —$R_5C(=S)SR_6$, —$R_5SO_3R_6$, —$SO_3R_6$, —$R_5N=C=S$, —$N=C=S$, —$NCO$, —$R_5$—$NCO$, —$CN$, —$R_5CN$, —$NNC(=S)R_6$, —$R_5NNC(=S)R_6$, —$NO_2$, —$R_5NO_2$, in the polar functional group, $R_5$ is linear or branched alkylene that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenylene that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynylene that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkylene that has 3 to 12 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; arylene that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; or alkoxylene that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; two or more $R_5$s are the same as or different from each other when two or more $R_5$s are present, and $R_6$, $R_7$, and $R_8$ are the same as or different from each other, and hydrogen; halogen; linear or branched alkyl that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkenyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; linear or branched alkynyl that has 2 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; cycloalkyl that has 3 to 12 carbon atoms and is substituted or unsubstituted with one or more substituent groups selected from the group consisting of halo- gen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; aryl that has 6 to 40 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy; or alkoxy that has 1 to 20 carbon atoms and is substituted or unsubstituted with one or more substituent groups selected from the group consisting of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl, and siloxy.

8. The polymer as set forth in claim 7, further comprising:
one or more selected from a repeating unit that is represented by the following Formula 10 and a repeating unit that is derived from a linear olefin:

<Formula 10> wherein p is an integer in the range of 0 to 4, and
R1', R2', R3', and R4' are each independently the same as the remainder other than the groups that are represented by Formula 2 among R1, R2, R3 and R4 defined by claim 7.

9. The polymer as set forth in claim 6, wherein the linear olefin comprises one or more selected from α-olefin, butadiene, and pentadiene.

10. A method of producing a polymer, the method comprising:
polymerizing a monomer comprising the cyclic olefin compound according to claim 1 at a temperature in the range of 10 to 200° C. in the presence of a catalyst mixture that comprises a precatalyst containing a transition metal of Group X and a cocatalyst providing a Lewis base being weakly coordinated with the metal of the precatalyst.

11. The method for producing a polymer as set forth in claim 10, wherein the precatalyst and the cocatalyst are mixed with each other at a molar ratio of 1:1 to 1:1000.

12. The method for producing a polymer as set forth in claim 10, wherein the catalyst mixture further comprises a compound containing a neutral electron donor ligand of Group XV.

13. The method for producing a polymer as set forth in claim 12, wherein the compound containing a neutral electron donor ligand of Group XV is represented by the following Formula 12:

[P(R)$_3$]    [Formula 12]

wherein R is any one selected from the group consisting of hydrogen; linear or branched alkyl or alkoxy having 1 to 20 carbon atoms; linear or branched alkenyl having 2 to 20 carbon atoms; substituted or unsubstituted cycloalkyl having 3 to 12 carbon atoms; substituted or unsubstituted aryl having 6 to 40 carbon atoms; substituted or unsubstituted aralkyl having 7 to 15 carbon atoms; and alkynyl having 2 to 20 carbon atoms, two or more Rs are the same as or different from each other when two or more Rs are present, and each of the groups can be substituted with halogen or haloalkyl having 1 to 20 carbon atoms.

14. The method for producing a polymer as set forth in claim 13, wherein the compound that contains the neutral electron donor ligand of Group XV comprises one or more selected from tricyclohexyl phosphine, triisopropyl phosphine, triphenyl phosphine, tri-t-butyl phosphine, and dicyclohexyl-t-butyl phosphine.

15. The method for producing a polymer as set forth in claim 10, wherein the precatalyst comprises one or more selected from $[(Allyl)Pd(Cl)]_2$, $[Pd(acetate)_2]$, $[NiBr(NPMe)_3]_4$, and $[PdCl(NB)OMe]_2$.

16. The method for producing a polymer as set forth in claim 10, wherein the cocatalyst comprises one or more selected from borane, borate, alkyl aluminum, and transition metal halide.

17. The method for producing a polymer as set forth in claim 16, wherein the cocatalyst comprises one or more selected from $B(C_6F_5)_3$, dimethylanilinium tetrakis(pentafluorophenyl)borate, methyl aluminoxane (MAO), triethyl aluminum $[Al(C_2H_5)_3]$, and $AgSbF_6$.

18. A liquid crystal alignment composition comprising the polymer according to claim 4.

19. A liquid crystal alignment film that is produced by using the liquid crystal alignment composition of claim 18.

20. A method for producing a liquid crystal alignment film, the method comprising:
applying a solution comprising the liquid crystal alignment composition of claim 18 on a substrate having a transparent electrode;
removing a solvent to form a film;
radiating ultraviolet rays that are polarized in a predetermined direction to provide the anisotropy on the surface of the film; and
curing the resulting film.

21. A liquid crystal display device comprising the liquid crystal alignment film of claim 19.

22. The polymer as set forth in claim 8, wherein the linear olefin comprises one or more selected from α-olefin, butadiene, and pentadiene.

23. A liquid crystal alignment composition comprising the polymer according to claim 7.

* * * * *